US012697214B2

(12) United States Patent
Costello et al.

(10) Patent No.: US 12,697,214 B2
(45) Date of Patent: Aug. 4, 2026

(54) PROSTHESIS DELIVERY DEVICE

(71) Applicant: Medtronic Vascular, Inc., Santa Rosa, CA (US)

(72) Inventors: Declan P. Costello, Ballinrobe (IE); Edmond G. Sheahan, Knocknacarra (IE); Aoife Monahan, Tubber (IE); Stephen A. Montgomery, Athenry (IE); Michael J. Deane, Belcare (IE); Michael Conerney, Tynagh (IE); Ciara S. Gallagher, Listowel (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 664 days.

(21) Appl. No.: 17/925,281

(22) PCT Filed: May 20, 2021

(86) PCT No.: PCT/US2021/033435
§ 371 (c)(1),
(2) Date: Nov. 14, 2022

(87) PCT Pub. No.: WO2021/242607
PCT Pub. Date: Dec. 2, 2021

(65) Prior Publication Data
US 2023/0346554 A1    Nov. 2, 2023

Related U.S. Application Data

(60) Provisional application No. 63/031,081, filed on May 28, 2020.

(51) Int. Cl.
*A61F 2/24* (2006.01)
*A61F 2/95* (2013.01)

(52) U.S. Cl.
CPC .......... *A61F 2/2436* (2013.01); *A61F 2/9517* (2020.05)

(58) Field of Classification Search
CPC ........ A61F 2/2427; A61F 2/2436; A61F 2/95; A61F 2/9517; A61F 2/9522; A61F 2/962;
(Continued)

(56) References Cited

U.S. PATENT DOCUMENTS

| | | | |
|---|---|---|---|
| 6,949,104 B2 | 9/2005 | Griffis et al. | |
| 9,192,495 B2 | 11/2015 | Dwork et al. | |

(Continued)

FOREIGN PATENT DOCUMENTS

| | | |
|---|---|---|
| EP | 3326583 | 12/2018 |
| EP | 3903744 A1 | 11/2021 |

(Continued)

OTHER PUBLICATIONS

International Search Report dated Aug. 24, 2021 in International Application No. PCT/US2021/033435.
(Continued)

*Primary Examiner* — Melanie R Tyson
(74) *Attorney, Agent, or Firm* — Wentsler LLC

(57) ABSTRACT

Techniques of this disclosure relate to delivery devices for use in delivering a prosthesis via percutaneous transcatheter (or transluminal) techniques. Embodiments achieve variable tensile and bending resistance of a transcatheter delivery device, which improves trackability and positioning accuracy of the system while maintaining the tensile characteristics of the transcatheter delivery device required for recapture and deployment of the prosthesis. Other embodiments relate to other components of a transcatheter delivery device that can be torqueable to assist in rotational positioning of the prosthesis. Other embodiments relate to the capsule of the transcatheter delivery device outer sheath member and/
(Continued)

or the prosthesis retention member of the transcatheter delivery device that can passively or otherwise rotate about their respective central axis to prevent built-up torque during delivery of a prosthesis. The capsule can include an echogenic marker. The aforementioned features and functionalities can be combined or utilized separately with delivery devices of the disclosure.

20 Claims, 16 Drawing Sheets

(58) Field of Classification Search
CPC .............. A61F 2/966; A61F 2002/9505; A61F 2002/9665; A61M 25/0102; A61M 25/0133; A61M 25/0136; A61M 25/0147; A61M 2025/0063
See application file for complete search history.

(56) References Cited

U.S. PATENT DOCUMENTS

| | | | | |
|---|---|---|---|---|
| 9,615,923 | B2 | 4/2017 | Creaven et al. | |
| 2012/0265296 | A1* | 10/2012 | McNamara | A61B 17/11 604/503 |
| 2012/0303111 | A1* | 11/2012 | Dwork | A61F 2/95 623/1.12 |
| 2014/0172003 | A1* | 6/2014 | Goepfrich | A61M 25/1034 606/192 |
| 2014/0343670 | A1* | 11/2014 | Bakis | A61F 2/2436 623/2.11 |
| 2015/0073539 | A1 | 3/2015 | Geiger et al. | |
| 2016/0220369 | A1* | 8/2016 | Chalekian | A61F 2/2436 |
| 2018/0256332 | A1 | 9/2018 | Gloss et al. | |
| 2018/0263772 | A1* | 9/2018 | Klima | A61F 2/2412 |
| 2021/0212808 | A1 | 7/2021 | Wu et al. | |

FOREIGN PATENT DOCUMENTS

| | | |
|---|---|---|
| WO | 2012009006 | 1/2012 |
| WO | 2015/038615 | 3/2015 |
| WO | 2018/006015 | 1/2018 |
| WO | 2019010303 | 1/2019 |
| WO | 2019233353 | 12/2019 |
| WO | 2021021368 | 2/2021 |

OTHER PUBLICATIONS

Extended European Search Report mailed Sep. 25, 2024 in European Patent Application No. 24183795.4.
Office action mailed Oct. 2, 2025 in European Patent Application No. 24183795.4.

* cited by examiner

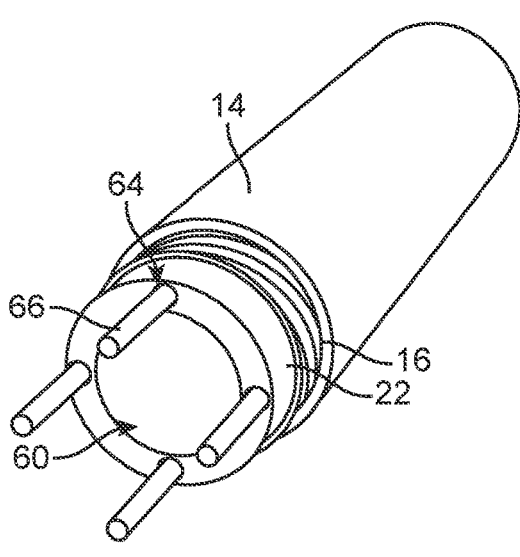
FIG. 10
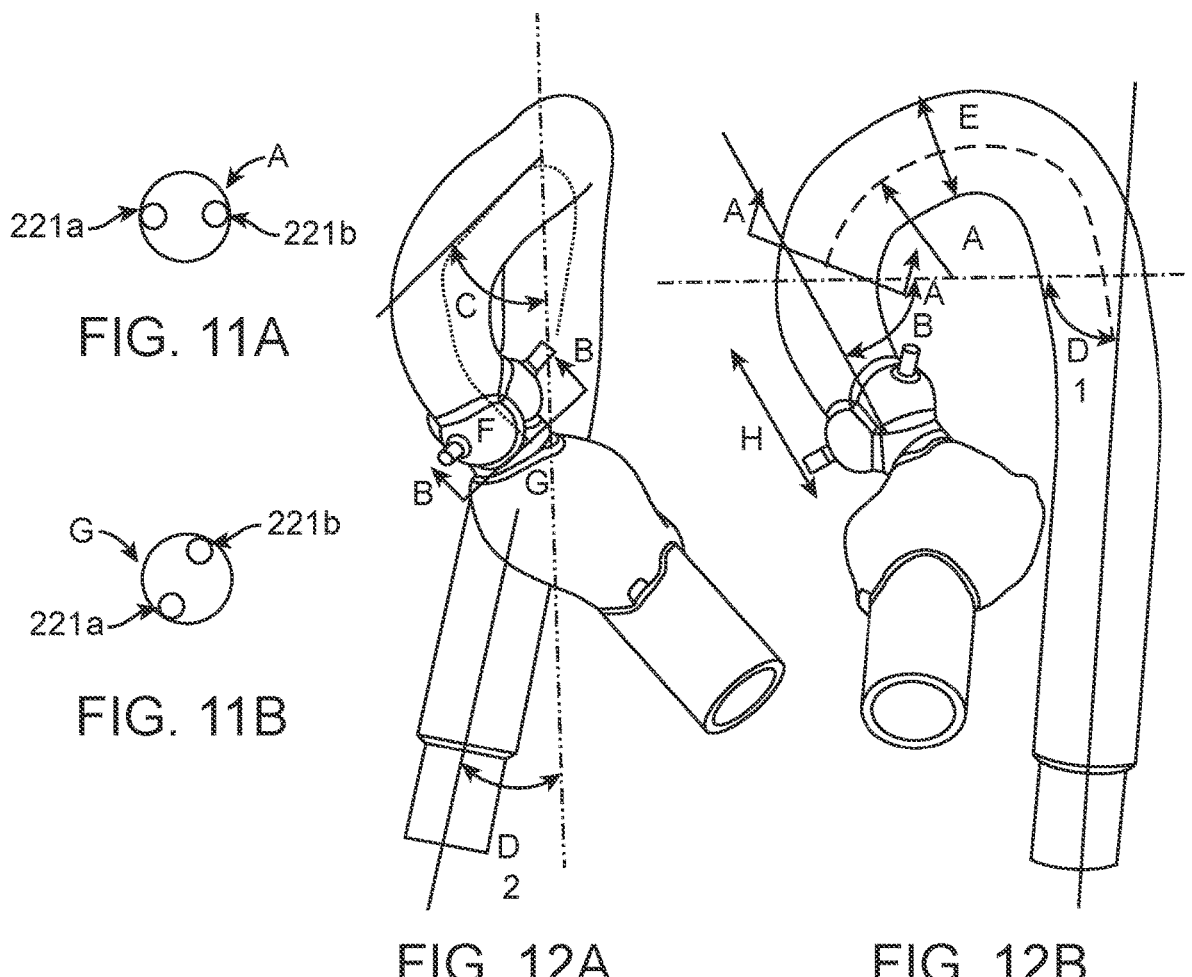
FIG. 11A
FIG. 11B
FIG. 12A
FIG. 12B

PROSTHESIS DELIVERY DEVICE

CROSS-REFERENCE TO RELATED APPLICATIONS

This is the National Stage under 35 U.S.C. § 371 of International Application No. PCT/US2021/033435, filed May 20, 2021, which claims the benefit of U.S. Provisional Patent Application No. 63/031,081, filed May 28, 2020, the entire content of which is incorporated herein by reference.

FIELD

The present technology is generally related to delivery devices for a prosthesis, such as a prosthetic heart valve.

BACKGROUND

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a transcatheter delivery device and then advanced, for example, through an opening in the femoral artery and through the descending aorta to the heart, where the prosthesis is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

A transcatheter delivery device must often navigate through tortuous anatomy as it is tracked through the vasculature to the treatment site within the heart. The transcatheter delivery device may be navigated through various anatomical turns as it travels within the vasculature. For example, a transcatheter delivery device may be navigated through the sharp bend of the aortic arch.

The present disclosure addresses problems and limitations associated with the related art.

SUMMARY

The techniques of this disclosure generally relate to delivery devices for use in delivering a prosthesis via percutaneous transcatheter (or transluminal) techniques. Various embodiments of this disclosure achieve variable tensile and bending resistance of a transcatheter delivery device, which improves trackability and positioning accuracy of the system while maintaining the tensile characteristics of the transcatheter delivery device required for recapture and deployment of the prosthesis as required during the procedure. Other various embodiments relate to other components of a transcatheter delivery device that can be torqueable to assist in rotational positioning of the prosthesis. Rotational positioning of the prosthesis can aid future percutaneous coronary intervention access, for example. Other various embodiments of the disclosure relate to the capsule of the transcatheter delivery device outer sheath member and/or the prosthesis retention member of the transcatheter delivery device that can passively or otherwise rotate about their respective central axis to prevent built-up torque during delivery of a prosthesis. The aforementioned features and functionalities can be combined or utilized separately with transcatheter delivery devices of the disclosure.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 10 is a partial, perspective view of an alternate shaft construction which may be used for the outer sheath member and torque coil of the disclosure.

FIG. 11A is a schematic diagram of a capsule of a torque coil, such as that of FIGS. 1, 5 and 10, having tensile capsule spines as the capsule is positioned at A-A of FIG. 12B.

FIG. 11B is a schematic diagram of the capsule and capsule spines of FIG. 11A, as the capsule is positioned at B-B of FIG. 12A.

FIGS. 12-12B are partial, schematic diagrams of a delivery path of the delivery device over an aortic arch and to a target site within a patient's heart.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Although the present disclosure has been described with reference to preferred embodiments, workers skilled in the art will recognize that changes can be made in form and detail without departing from the spirit and scope of the present disclosure.

Figure 20:
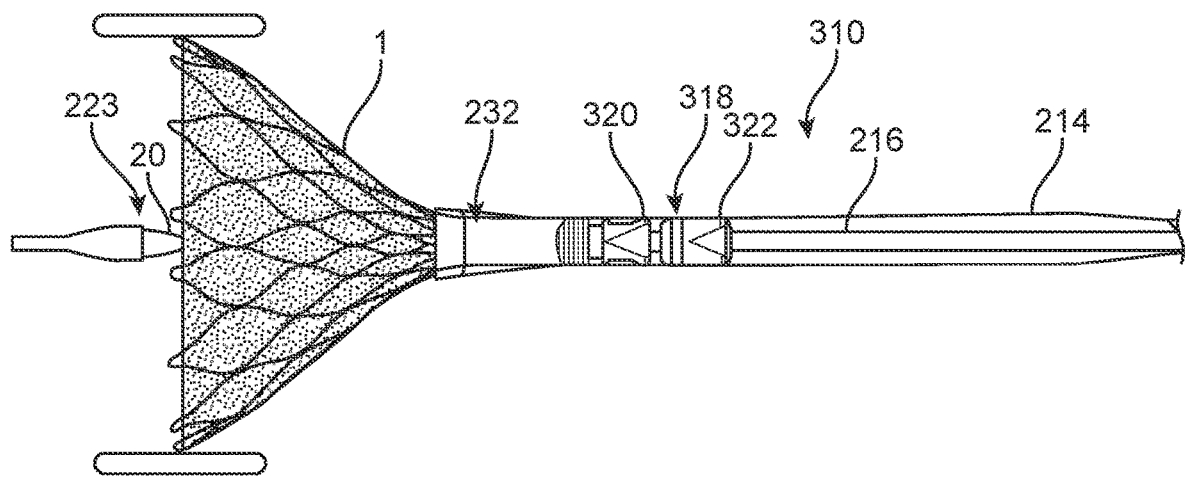
FIG. 20 is a partial, side view of an alternate delivery device having a spindle that is rotatable (an outer sheath member of the delivery device is shown as transparent for ease of illustration).
Figure 21:
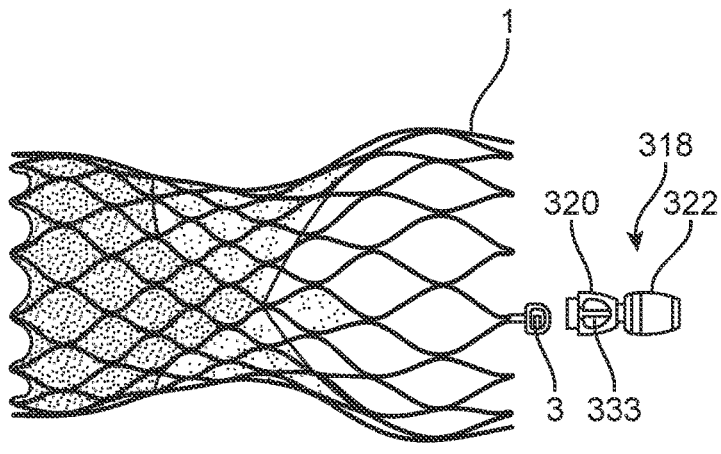
FIGS. 21-22 are side views of the spindle and a prosthesis, which can be maintained and releasably secured to the delivery device of FIG. 13 with the spindle.
Figure 22:
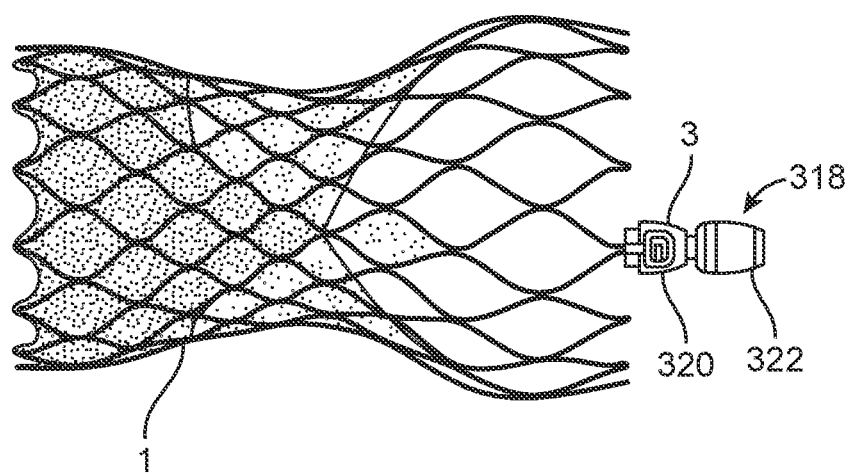
Figures 23A, 23B:
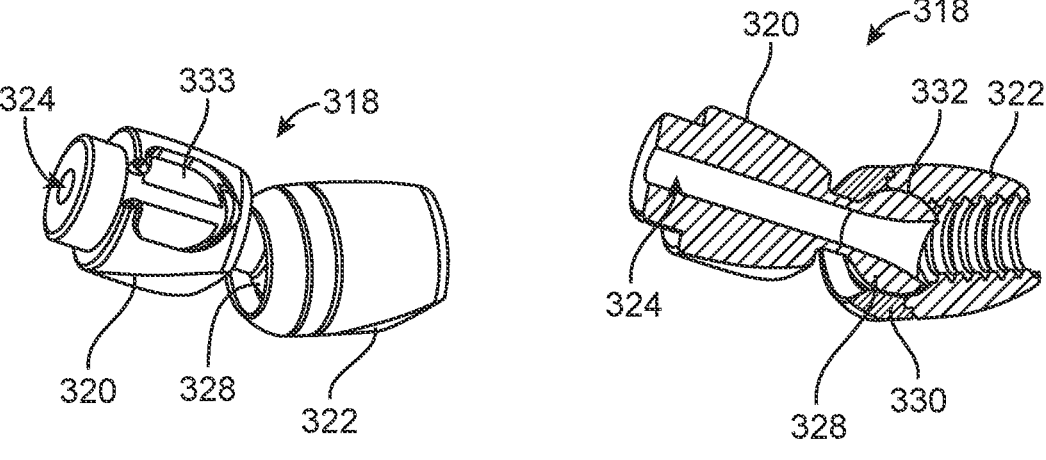
FIG. 23A is a perspective view of the spindle of FIGS. 20-22.
FIG. 23B is a cross-sectional view of the spindle of FIG. 23A.
Figure 24:
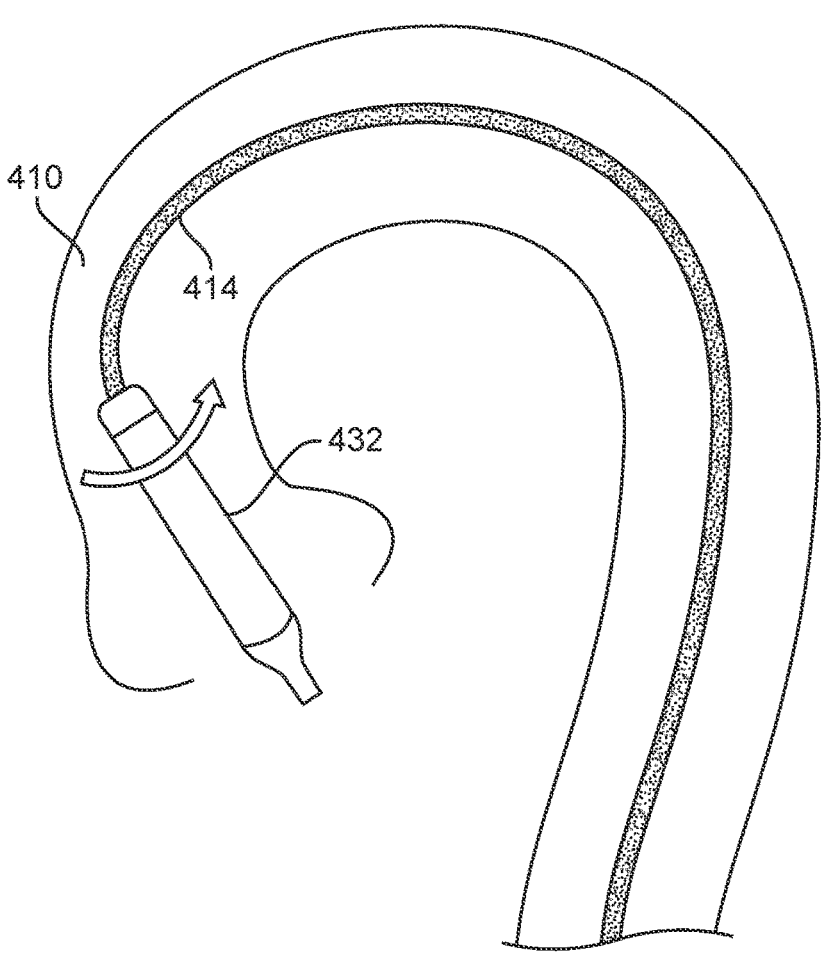
FIGS. 24-27 collectively illustrate an alternate delivery device having a capsule and a spindle that can rotate.
Figure 25:
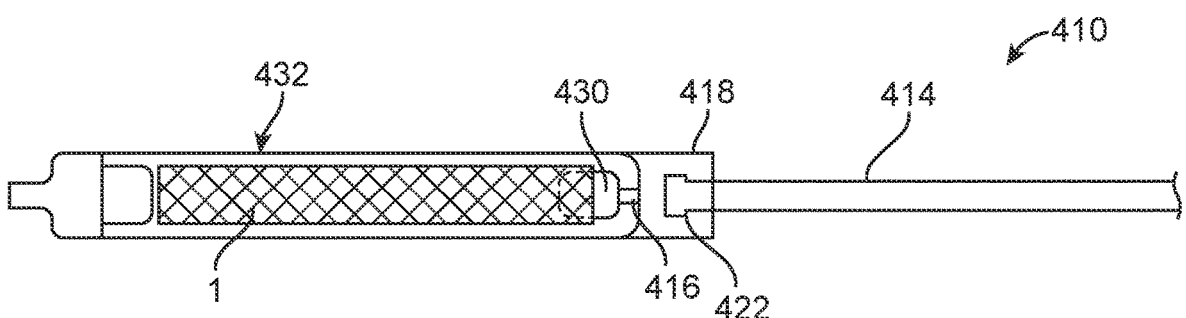
Figure 26:
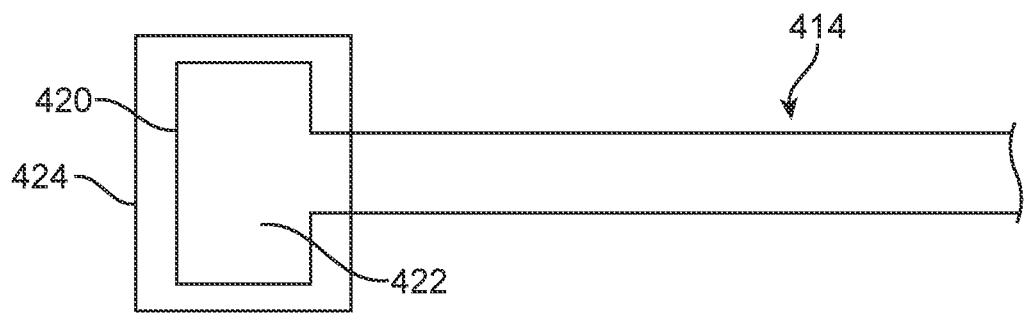
Figure 27:
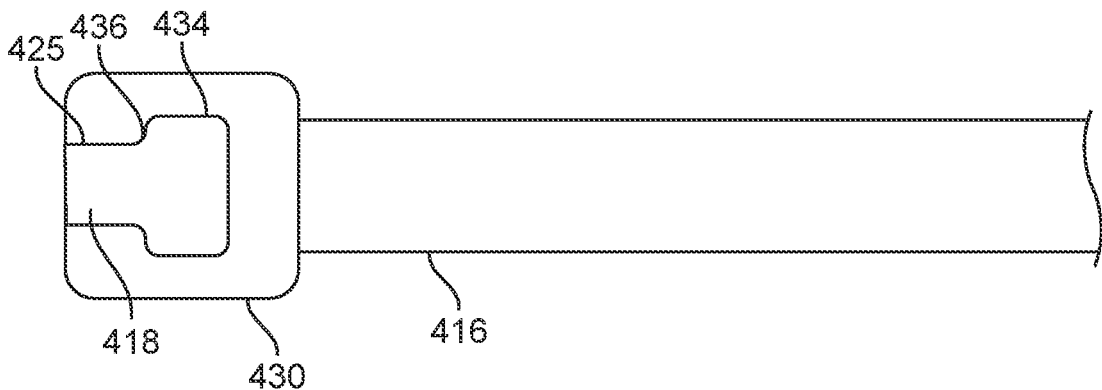

FIGS. 1-6 collectively illustrate an example of a delivery device 10 of the present disclosure. Generally, the delivery device 10 can include a handle assembly 12, an outer sheath member 14, an inner shaft member 16, and a prosthesis retention member, hub, or spindle 18 positioned over or connected to the inner shaft member 16. Prosthesis retention member 18 is configured to support a prosthesis (e.g., a stent or stented prosthetic heart valve; FIGS. 20-22 illustrate one example). The outer sheath member 14 and the inner shaft member 16 can be supported and/or actuated with the handle assembly 12 as will be discussed below in greater detail.

Figure 1:
FIG. 1 is a partial, perspective view of a handle assembly of a delivery device.

The outer sheath member 14 is made of a flexible and tubular body 28 and has a proximal end 30*a* and a distal end 30*b*. The proximal end 30*a* is connected to the handle assembly 12 and the distal end 30*b* can optionally be connected to a capsule 32 for sheathing the prosthesis. In instances where a distinct capsule is not provided, the distal end 30*b* of the outer sheath member 14 can be long enough to sheathe a prosthesis secured to the prosthesis retention member 18 and optionally long enough to further cover at least a portion of a tip member 23 connected to an inner support member 20. In some embodiments, the inner support member 20 and inner shaft member 16 may be continuous or may not be continuous and can be linked with one or more elements as discussed in greater detail below. The delivery device 10 can also include an outer sheath member actuator 34 (generally referenced in FIGS. 1-2) provided in the handle assembly 12 or otherwise at a proximal end 30*a* of the outer sheath member 14 to control proximal/distal movement of the outer sheath member 14 to sheath/unsheathe the prosthesis for deployment and/or recapture of the prosthesis. One example is illustrated in FIG. 1. In this example, the outer sheath member actuator 34 is configured to slide proximally and distally with respect to a first portion 13*a* of the handle assembly 12 to correspondingly move the outer sheath member 14 proximally and distally with respect to handle assembly 12.

Extending within a lumen of the outer sheath member 14 is the inner shaft member 16 that extends from the handle assembly 12 to the prosthesis retention member 18. Various embodiments are configured such that the inner shaft member 16 is torqueable (i.e. rotatable) about a longitudinal axis of the inner shaft member 16. Rotational movement of the inner shaft member 16 can be provided with an inner shaft member actuator 40 that can be provided in the handle assembly 12. In one example shown in FIGS. 1-3, the inner shaft member actuator 40 is a bevel gear that includes a dial 42 (generally referenced) having a plurality of teeth 43 that are configured to engage a plurality of teeth 45 of a hub 44 that is set within a second portion 13*b* of the handle assembly 12 and rotatable about an axis perpendicular to a longitudinal axis of the second portion 13*b*. The second portion 13*b* defines an opening 46 in which the respective teeth 43, 45 are housed. As the dial 42 is rotated by a user, the dial teeth 43 engage and push the hub teeth 45, which rotates the hub 44 to correspondingly rotate inner shaft member 16 about its longitudinal axis.

In one example, the inner shaft member 16 and the prosthesis retention member 18 are fixedly secured (e.g., via welding or the like) so that rotation of the inner shaft member 16 translates to rotation of the prosthesis retention member 18. In one embodiment, the inner shaft member 16 is made from a triple layer helical hollow-core shaft tube in which multiple flat steel wires are helically wound together tightly to form a hollow-core or lumen. Such outer sheath member inner shaft member 16 has high torque and compression resistance while maintaining minimal bending stiffness (relative to the entire delivery device).

Figure 6:
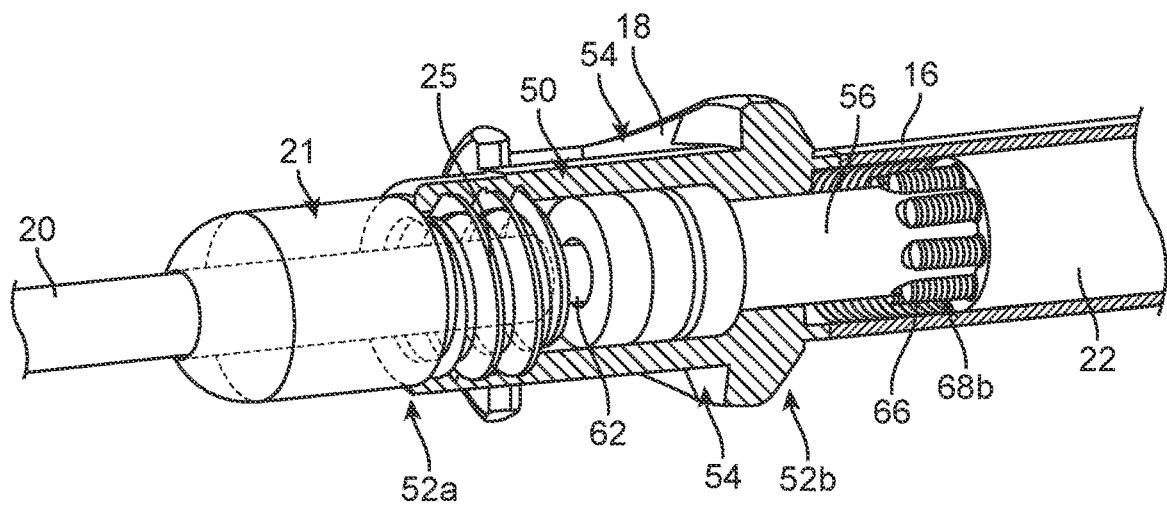
FIG. 6 is a partial, cross-sectional view of a prosthesis retention member, which is connected to the inner shaft member and the core member of FIG. 5.

In one example, which is perhaps best shown in FIG. 6, the prosthesis retention member 18 includes a body 50 having a distal end 52*a* and a proximal end 52*b* (see, in particular, FIG. 6). The body 50 defines one or more pockets 54 configured to engage the prosthesis during delivery. The inner support member 20 can optionally extend from the distal end 52*a* of the prosthesis retention member 18 with an inner support member attachment 21 and can terminate at a conically-shaped tip member 23. In one example, the prosthesis retention member 18 includes a coupling 56 positioned within a cavity of the body 50. In various embodiments, the inner support member attachment 21 has a threaded portion 25, which engages the prosthesis retention member 18. In one example, the body 50 is configured such that it can freely rotate about a longitudinal axis of the coupling 56.

In one example, the inner shaft member 16 is positioned within a lumen of the outer sheath member 14 and can be secured to the prosthesis retention member 18. In one example, the inner shaft member 16 is made from a polymer material. The inner shaft member 16, which can include one or more lumens, can be configured to rotate with respect to the outer sheath member 14. The outer sheath member 14 can be configured to slide or move back and forth longitudinally with respect to the inner shaft member 16. For example, as perhaps best shown in FIG. 5, the inner shaft member 16 can include a central lumen 60 for receiving an optional core member 22. The inner shaft member 16 is configured such that it can freely rotate about a longitudinal axis of the core member 22. The core member 22 can define a plurality of outer lumens 64 (generally referenced) extending circumferentially around an optional central lumen 60 to slidably receive a guide wire 62. The outer lumens 64 can be configured to each slidably receive a tensile wire 66 (generally referenced for ease of illustration). As shown, the inner shaft member 16 includes eight outer lumens 64 and one central lumen 60. In other examples, the central lumen 60 may be omitted. In other examples, the number of outer lumens 64 may vary. Each of the tensile wires 66 has a proximal end 68a and a distal end 68b (only one tensile wire 66 is labeled for ease of illustration, see FIGS. 3, 5 and 6). The proximal end 68a is secured within the handle assembly 12 and the distal end 68b is fixedly secured to a coupling 56 of the prosthesis retention member 18 via welding or the like. In this way, movement of the tensile wires 66 can cause the prosthesis retention member 18 and the inner support member 20 to actively deflect. In one example, as is perhaps best shown in FIG. 3, tension in each tensile wire 66 can be maintained with an optional biasing element 70, e.g., a compression spring or the like threaded over each tensile wire 66. Each tensile wire 66 can include a bulbous portion 72 at its proximal end to 68a maintain the spring 70. Opposite the bulbous portion 72, each spring 70 can be maintained against a retaining plate 74 through which the tensile wires 66 are threaded via slots 76.

Generally, the delivery device 10 can be configured so that the tensile wires 66 can provide selective tensile resistance or rigidity and bending stiffness or resistance to the core member 22 outer sheath member. In this way, the handle assembly 12 includes a tensile resistance actuator 80 that can selectively engage the tensile wires 66 to restrict movement of the tensile wires 66 and thus, increase the tensile resistance of the core member 22 outer sheath member. Generally, the delivery device 10 has an unlocked configuration in which a length of the tensile wire 66 between the coupling 56 and the tensile resistance actuator 80 is variable and also the delivery device 10 has a locked configuration in which the length of each tensile wire 66 between the coupling 56 and the tensile resistance actuator 80 is invariable. In the unlocked configuration, a length of each tensile wire 66 between the coupling 56 and the tensile resistance actuator 80 is generally free to change during bending of the core member 22 and the inner shaft member 16. The inside of a curve is the shortest path so the tensile wires 66 will want to extend further out of a proximal end 17 of the core member 22 (FIG. 4) as the distal ends of the tensile wires 66 are fixedly secured to the coupling 56. The outside of the curve is the longest path so the tensile wires 66 will want to retreat into the core member 22. This configuration makes the construction flexible. The flexible modulus is practically zero in some embodiments so that the tensile wires 66 will not resist bending. In one embodiment, each of the tensile wires 66 are continually tensioned in the unlocked configuration with the biasing element 70, for example to remove slack in each of the tensile wires 66. The tensile resistance actuator 80 can take many configurations. In one example, which is perhaps best shown in FIGS. 3-4, the tensile resistance actuator 80 includes a support 82 positioned within the third portion 13c of the handle assembly 12. The support 82 can have an outer surface 84 over which the tensile wires 66 are positioned. In one example, the tensile wires 66 are equally spaced around a circumference of the support 82. In one embodiment, the outer surface 84 includes a corresponding groove in which one tensile wire 66 is positioned and maintained. In some examples, the outer surface 84 can at least be partially tapered in a direction of the first portion 13a. The tensile resistance actuator 80 further includes a collar 86 positioned at least partially around the support 82 and a lever 88 engaged with the collar 86. In one example, the lever 88 includes a plurality of slots 89 engaged with respective pins 87 extending from the collar 86 (only one pin 87 is visible in FIG. 3). When the lever 88 is in an upright position (FIGS. 3-4), the collar 86 is in a distal position (FIG. 4), disengaged from the support 82, so that the tensile wires 66 are in the unlocked configuration and can slide with respect to the collar 86 and the portion 13c due to forces applied by the bending and straightening of core member 22. When the lever 88 is pushed down toward the third portion 13c, the collar 86 is pushed proximally to engage the support 82 and the tensile wires 66 to restrict longitudinal movement of the tensile wires 66 so that the tensile wires 66 cannot move proximally or distally relative to the collar 86 or with respect to the third portion 13c in response to forces applied by the core member 22. The support 82 can include an aperture or lumen (FIG. 3) through which the guide wire 62 can be routed and moved distally or proximally regardless of the position of the lever 88. It is further envisioned that the support 82 can include one or more protrusions 83 corresponding with one or more recesses 85 in the collar 86 to maintain alignment of the support 82.

Figure 7:
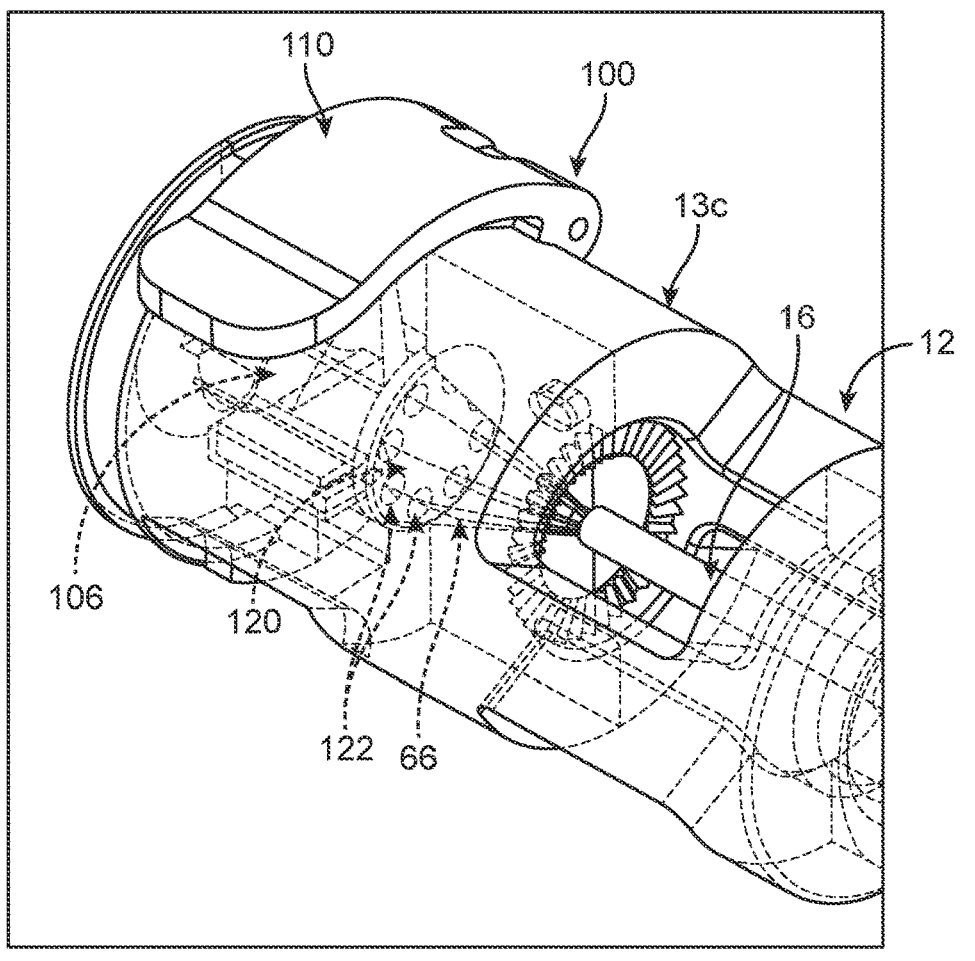
FIGS. 7-9 illustrate an alternate actuator that can be provided in the handle assembly to lock and unlock the tensile wires.
Figure 8:
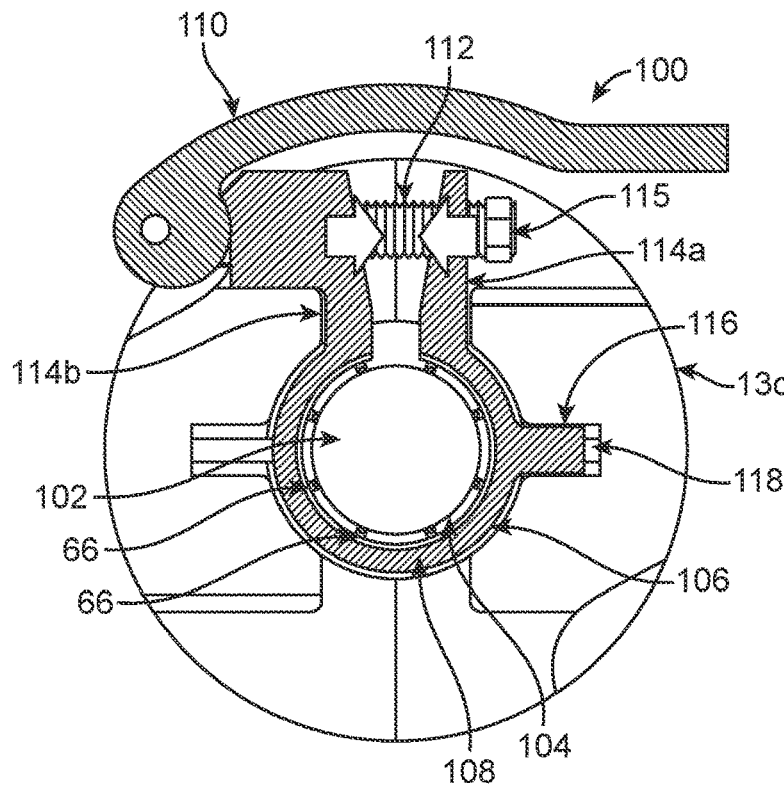
Figure 9:
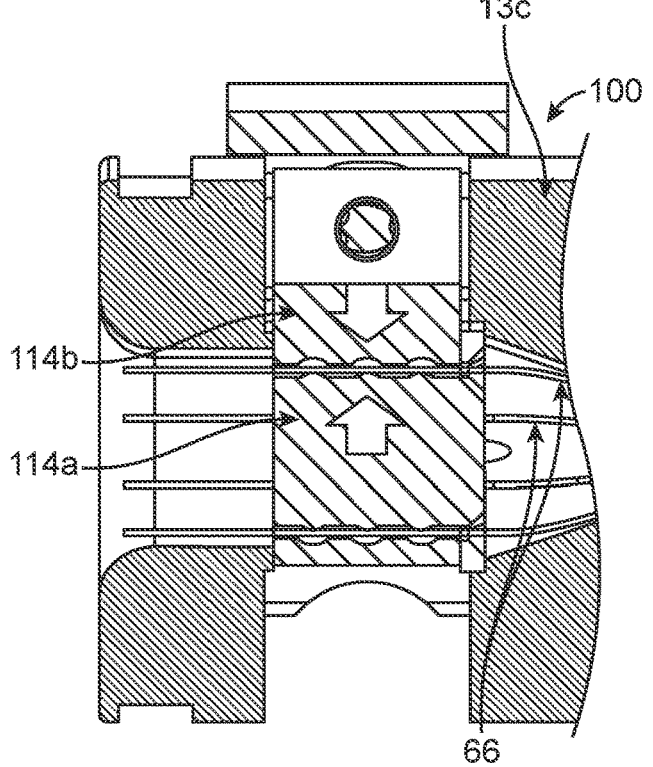
Figure 13:
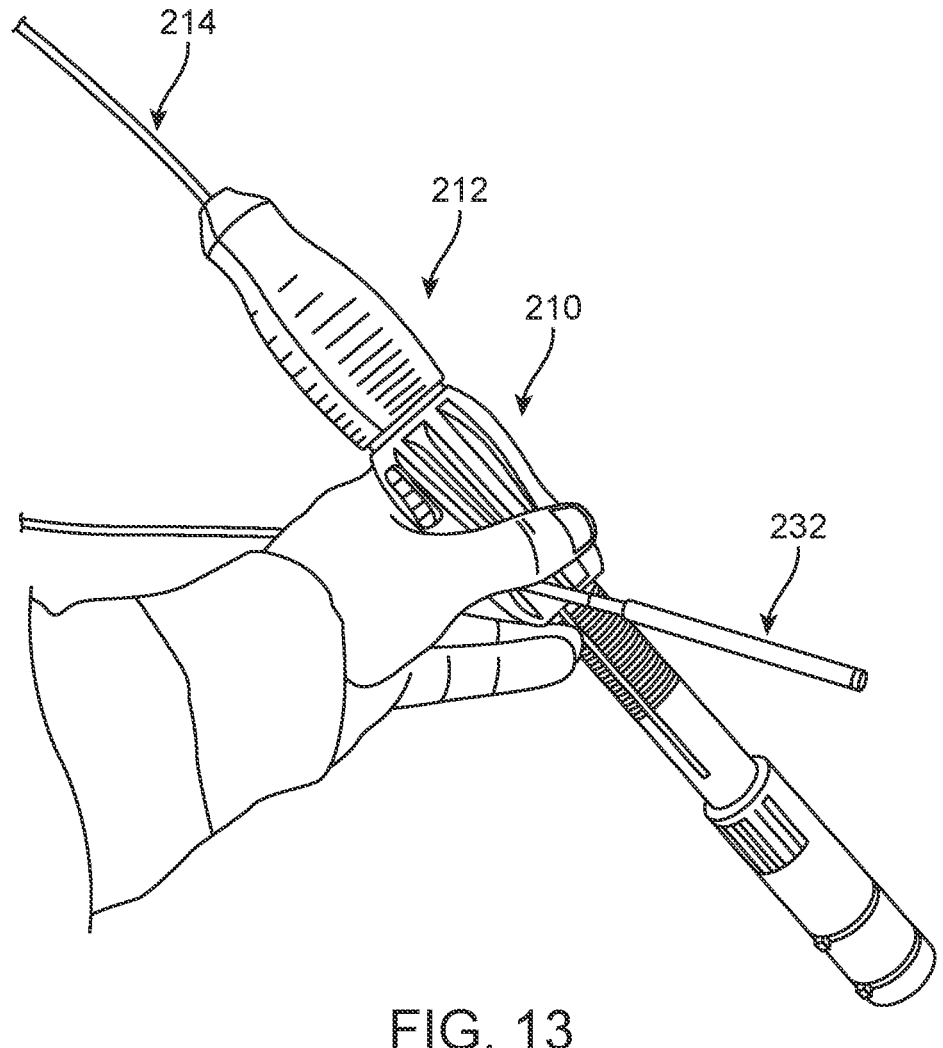
FIG. 13 is a partial, side view of an alternate delivery device configured to have a rotating capsule and a rotating spindle.

Another example of a suitable tensile resistance actuator 100 is illustrated in FIGS. 7-9. In this example, the tensile resistance actuator 100 is arranged similar to and functions similar to a quick-release post clamp. For example, the tensile resistance actuator 100 includes a cylindrical support 102 positioned within the third portion 13c of the handle assembly 12. The support 102 can have an outer surface 104 over which the tensile wires 66 (generally referenced) are positioned. As with the prior embodiment, the tensile wires 66 can at least partially be maintained within grooves (not shown) provided within the support 102. In one example, the tensile wires 66 are equally spaced around a circumference of the support 102. The tensile resistance actuator 100 further includes a collar 106 having an arcuate clamping portion 108 positioned at least partially around the support 102 and a lever 110 engaged with the collar 106. The collar 106 is configured to be biased outwardly (i.e. in a direction that increases the distance between legs 114a, 114b and increases an inner diameter of the clamping portion 108). The lever 110 is connected to a screw 112, which is also engaged by one leg 114a of the collar 106 and is positioned through a clearance aperture (not visible) in the second leg 114b of the collar 106 and secured with a nut 115. In this embodiment, the lever 110 is configured to rotate toward and away from the third portion 13c at an angle of approximate 90 degrees with respect to a central axis of the third portion 13c. When the lever 110 is in an upright position, the clamping portion 108 is free to expand to its normal state having an increased inner diameter, which is sufficiently large to disengage the tensile wires 66 so that the tensile wires 66 can move distally past the clamping portion 108.

When the lever 110 is pushed down toward the third portion 13c as is shown in FIGS. 7-8, the legs 114a, 114b are pushed toward each other so that an inner diameter of the clamping portion 108 is reduced to engage tensile wires 66 to restrict longitudinal movement of the tensile wires 66 so that the tensile wires 66 cannot move distally or proximally relative to the clamping portion 108. In one example, the collar 106 can include a protrusion 116 and the third portion 13c can include a pocket 118 in which the protrusion 116 slides as the collar 106 transitions between the locked and unlocked configurations. As with the previous embodiment, the support 102 can include an aperture or lumen (not shown) through which a guide wire can be routed and moved distally or proximally regardless of the position of the lever 110. To keep the tensile wires 66 separated and spaced, the tensile wires 66 can be routed through a guide 120 having a plurality of alignment apertures 122, the guide 120 being positioned adjacent and distal to the support 102 as shown in FIG. 7, for example. It is to be understood that the tensile resistance actuator 100 can be incorporated into any delivery device disclosed herein and utilized with any other complimentary features disclosed herein.

Referring now to FIG. 10, which illustrates an alternate outer sheath member 14 and an alternate inner shaft member 16 for use with the delivery device 10 or other delivery devices disclosed herein. In this example, the inner shaft member 16 can include an optional core member 22 defining four outer lumens 64 extending circumferentially around an optional central lumen 60 to slidably receive a guide wire 62. The four outer lumens 64 can be configured to each slidably receive a tensile wire 66 (only one outer lumen 64 and tensile capsule spines 66 are referenced for ease of illustration). In one example, the outer lumens 64 are equally spaced about a circumference of the core member 22.

Referring now to FIGS. 11A-15, which collectively illustrate an alternate delivery device 210, having components that can be integrated into other delivery devices disclosed herein. The delivery device 210 includes a handle assembly 212 connected to an inner support member 220 supporting a prosthesis retention member, hub, or spindle 218, which is configured to engage and maintain a prosthesis (such as prosthesis 1 shown in FIGS. 20-22). In one example, an inner shaft member 216 is screwed or otherwise fixedly secured to the prosthesis retention member bearing 213 to allow the prosthesis retention member 218 to freely rotate relative to the inner shaft member 216. Optionally, the delivery device 210 can include an outer sheath member 214. The outer sheath member 214 can define one or more outer lumens 64 extending circumferentially around an optional central lumen to slidably receive an inner shaft member 216. The outer lumens 64 can be configured to each slidably receive a tensile wire 66. In one example, the outer lumens 64 are equally spaced about a circumference of outer sheath member 214. Outer sheath member 214 can be configured so that the tensile wire 66 can provide selective tensile resistance or rigidity and bending stiffness or resistance to the outer sheath member 214. The outer sheath member 214 can be made of a flexible and tubular body 228 and has a proximal end and a distal end. The proximal end can be connected to the handle assembly 212 and the distal end can optionally be connected to a capsule 232 for sheathing the prosthesis. In instances where a distinct capsule is not provided, the distal end of the outer sheath member 214 can be long enough to sheathe a prosthesis secured to the prosthesis retention member 218 and optionally long enough to further cover at least a portion of a tip member 223 connected to an inner support member 220. The delivery device 210 can also include an outer sheath member actuator provided in the handle assembly 212 or otherwise at a proximal end of the outer sheath member 214 to control proximal/distal movement of the outer sheath member 214 to sheath/unsheathe the prosthesis for deployment and/or recapture of the prosthesis. The outer sheath member 214 can be configured to rotate relative to inner shaft member 216. It is envisioned that the delivery device 210 can be configured to have a rotatable prosthesis retention member 218 to release built-up torque energy that can be exacerbated by the rotation of capsule 232 and/or outer sheath member 214 relative to inner shaft member 216.

In some capsules of the disclosure, the capsule 232 will include two tensile capsule spines 221a, 221b (schematically represented in FIGS. 11A-11B) embedded within a material forming of capsule 232. The tensile capsule spines 221a, 221b being 180 degrees from each other and extending substantially along a length of the capsule 232. Due to the tensile capsule spines 221a, 221b, which provide the capsule 232 strength when the prosthetic valve is loaded into the capsule, the capsule 232 can only bend in one plane. It is envisioned that the delivery device 210 can be configured to have a rotatable spindle 218 to release built-up torque energy that can be exacerbated by the tensile capsule spines 221a, 221b, when present. As schematically depicted in FIGS. 11A-12B, when delivery device 210 is traveling around an aortic arch, the tensile capsule spines 221a, 221b will naturally try to position themselves as close to the outer wall of the bend/arch A in the vasculature, as possible. In order for the delivery device 210 to advance to an annulus, the plane of angulation changes, therefore, the tensile capsule spines 221a, 221b will twist from the position of FIG. 11A to the position of FIG. 11B. This orientation will add torque in the system (i.e. delivery device 210). Once the prosthesis is positioned within and engaged with the annulus on initial deployment of the prosthesis and, as the capsule 232 (or outer sheath member 214 is retracted), an amount of torque will be added to the delivery device 210 because of the untwisting of the tensile capsule spines 221a, 221b. This torque energy is a potential additional energy which the system releases upon deployment, which can negatively affect accuracy in the deployment position of the prosthesis. In various embodiments where the prosthesis retention member 218 is rotatable, as the capsule 232 is retracted prior to deployment, the prosthesis retention member 218 will reorient itself releasing at least most of this tension before deployment of the prosthesis, thus increasing deployment accuracy.

Figure 14:
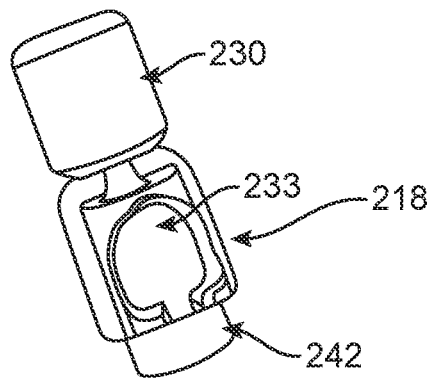
FIG. 14 is a side view of the spindle that can be incorporated into the delivery device of FIG. 1 or FIG. 13.
Figure 15:
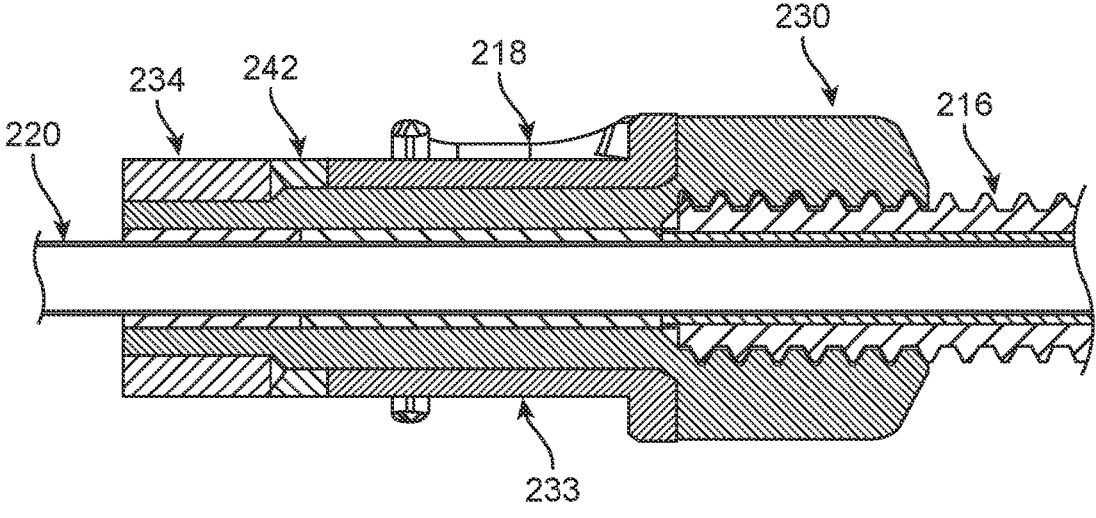
FIGS. 15-16, schematically illustrate select components of the delivery device of FIG. 13 that allow for the capsule and spindle to rotate.

Examples of a rotatable prosthesis retention member 218 are shown in detail in FIGS. 14-15. In these examples, the rotatable prosthesis retention member 218 fits over a bearing chassis 230 that is screwed to the inner shaft member 216. The bearing chassis 230 is rigidly affixed to the inner shaft member 216 so the inner shaft member 216 cannot rotate with respect to the bearing chassis 230. In one example, the prosthesis retention member 218 slides over the bearing chassis 230 and can spin freely with respect to the bearing chassis 230 and the inner shaft member 216. A retaining cap 242 can be welded or otherwise fixedly secured to the bearing chassis 230, which maintains the prosthesis retention member 218 in longitudinal position. The prosthesis retention member 218 can further include a rest member or pockets 233 that can act as a rest for paddles 3 of the prosthesis 1 (see also, FIG. 21, which illustrates the prosthesis 1). In another example, the rest member 233 could be configured as an extension of the welded retaining cap 242.

Figure 16:
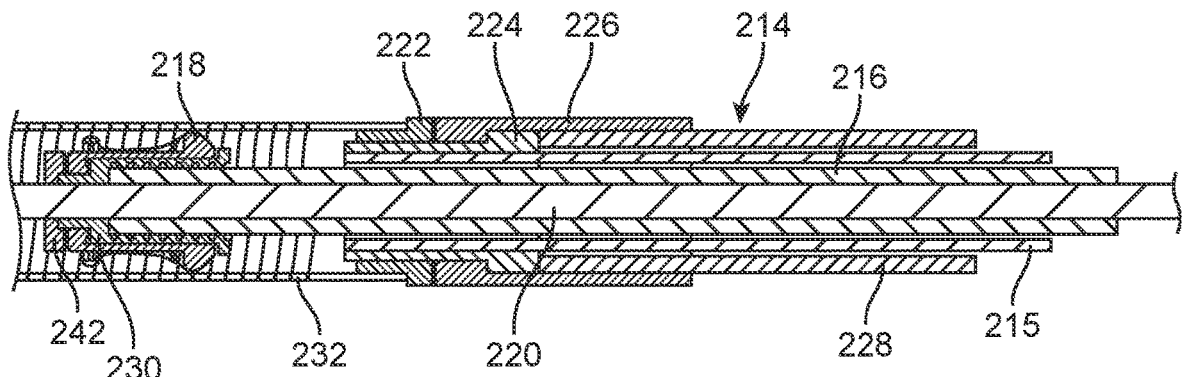

Another example of an outer sheath member 214 (FIG. 16) for use in an alternative delivery device 10 includes a rotatable capsule 232. Outer sheath member 214 includes a capsule mount 222 that interconnects the capsule 232 to a capsule bearing 224 that is rotatably engaged with a retainer 226 connected to a flexible, tubular body 228 of the outer sheath member 214. In one embodiment of the delivery device 10, the outer sheath member 214 is configured to slide or move back and forth longitudinally with respect to the inner shaft member 216 and the inner shaft member 216 is configured such that it can freely rotate about a longitudinal axis of the outer sheath member 214. In a prosthesis delivery configuration, rotation of the inner shaft member 216 of the delivery device 10 will rotate the prosthesis retention member 218 thereby rotating a prosthesis coupled to the prosthesis retention member 218. Rotation of the prosthesis within the capsule 232 can rotate the capsule 232 relative to the tip member 223 of outer sheath member 214. The prosthesis in a delivery configuration can rotate the freely rotating capsule 232 due to friction between the prosthesis sheathing capsule 232 and the compressed or compacted prosthesis for delivery coupled to the prosthesis retention member 218.

It is envisioned that in embodiments where the capsule is configured to rotate, the capsule can be connected to the outer sheath member with a coupling that enables passive rotation with the prosthesis and prosthesis retention member. This functionality also reduces tracking force in tortuous anatomies as resistance to torqueing can be "turned off" (i.e. allow the actuator to free-wheel during tracking of the outer sheath member). It is envisioned that in some embodiments, the prosthesis retention member is rotatable relative to the inner shaft member while the capsule is fixed relative to the outer sheath member. It is envisioned that in some embodiments, the capsule is rotatable relative to the outer sheath member while the prosthesis retention member is fixed relative to the inner shaft member. It is envisioned that in some embodiments, the prosthesis retention member is rotatable relative to the inner shaft member and the capsule is rotatable relative to the outer sheath member.

Figure 17A:
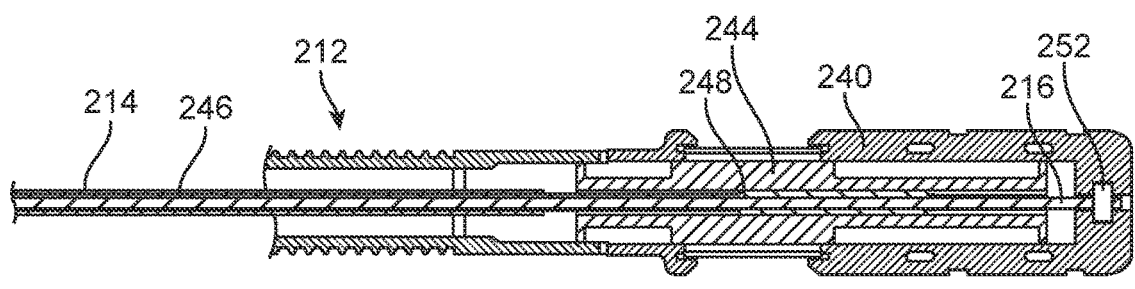
FIGS. 17A-18 are cross-sectional illustrations of a handle assembly of the delivery device of FIG. 13.
Figure 17B:
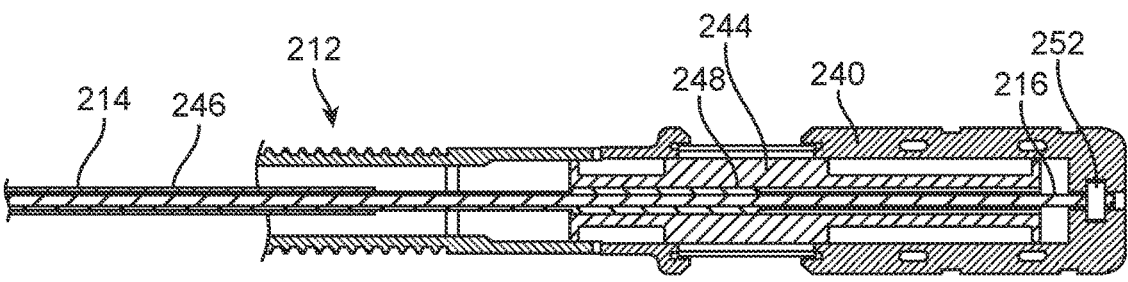
Figure 18:
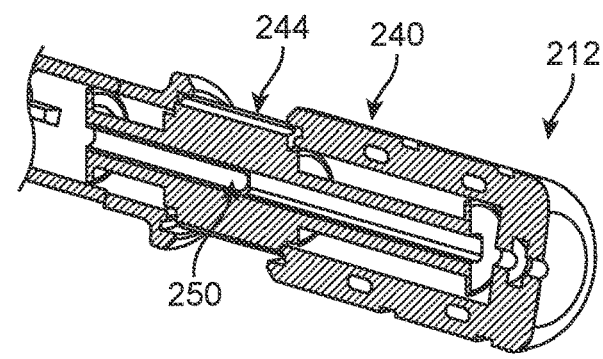

An example of one suitable handle assembly 212 for the delivery device 210 is shown in greater detail in FIGS. 17A-18. Handle assembly 212 includes a body 240 that receives and maintains the inner shaft member 216 and outer sheath member 214. The body 240 may be a unitary structure or many comprise multiple components pieced together. Additional shafts, such as a torque coil disclosed above, can also be maintained, if provided. The inner shaft member 216 can be retained and fixed within the body 240 with a retainer 252 provided in the body 240. A capsule actuator 244 is provided within the body 240 and is configured to control longitudinal movement of the outer sheath member 214 and capsule 232 to withdraw and recapture the prosthesis, as desired. In handle assembly 212, if provided, torque coil 246 can be bonded to a coil shuttle 248. The coil shuttle 248 has a profile that allows the coil shuttle 248 to slide axially distally and proximally along a longitudinally axis of the handle assembly 212 within the capsule actuator 244 as the capsule actuator 244 is rotated about a longitudinal axis of the body 240. Therefore, the capsule actuator 244 defines a lumen 250 that has a profile corresponding to the coil shuttle 248. In one example, the profile is a polygon (e.g., a square) so that the coil shuttle 248 can move longitudinally but cannot rotate about the longitudinal axis of the coil shuttle 248. This allows for the capsule 232 and coil shuttle 248 to move axially as the capsule 232 is retracted. Therefore, the capsule actuator 244 has a length to allow the coil shuttle 248 to move during capsule 232 retraction from the prosthesis without disengaging from its rotary constraint. It should be understood that the delivery device 210 shown in FIGS. 17A-18 can be configured similarly to other delivery devices disclosed herein except as explicitly stated.

Figure 19:
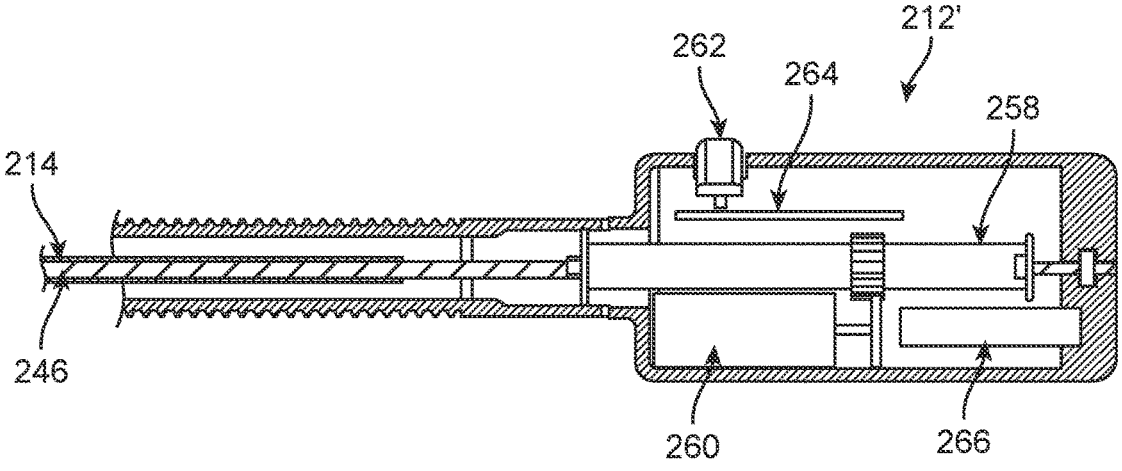
FIG. 19 is a cross-sectional illustrations of an alternate handle assembly.

FIG. 19 illustrates an alternate handle assembly 212'. The handle assembly 212' is operated in the same way as the handle assembly 212 of FIGS. 17A-18 with the exception that the handle assembly 212' is driven with a motor and has potential to remove the slack of the system allowing for a more accurate torque response. In this embodiment, a torque coil driver 258 provided in the handle assembly 212' is driven by a motor assembly (including at least a motor and a gearbox assembly) 260 and which is selectively user actuated by a motor actuator 262, such as a rocker wheel, push button, slider, or the like. This motor actuator 262 interfaces with a controlling printed circuit board assembly (PCBA) 264 which controls the motion of the motor assembly 260. The motor assembly 260 may or may not include a torque sensor. In embodiments containing the torque sensor, after user actuation of the motor actuator 262, the motor assembly 260 will actuate until a baseline torque load is reached. This baseline torque is enough to remove slack from the torque coil 246. Once this baseline torque value is reached, the motor will continue to rotate giving close to a 1:1 response ratio of the coil rotation at the distal end of the device when rotated at the proximal end. Examples of the user interface may be a push button, where the first press of the button removes the slack from the torque coil 246 and each subsequent press rotated the torque coil 246 by a predetermined number of degrees (e.g., 1 or more degrees). In other embodiments, the motor actuator 262 may be a wheel or rotary actuator where upon turning the wheel, the slack is removed after which the torque coil 246 is rotated by the same rotation angle as the rotary motor actuator 262. Other motor actuators and user interfaces are also envisioned. One significant advantage of electromechanical actuation is that any slack of the torque coil 246 can potentially be removed resulting in a more accurate device. The motor assembly 260 can be powered in numerous conventional ways. In one example, the handle assembly 212' includes a battery 268 for powering the motor assembly 260.

Referring now in addition to FIGS. 20-23B, in another embodiment, a delivery device 310 can include an alternatively configured prosthesis retention member, hub or spindle 318 configured to be rotatable and deflectable with respect to inner shaft member 216 about a longitudinal axis of the inner shaft member 216. In this example, the prosthesis retention member 318 includes a distal portion 320 rotatably connected to a proximal portion 322. The distal portion 320 has an aperture 324 for receiving and maintaining the inner support member 20 as well as pockets 333 for receiving and maintaining paddles 3 or other components of the prosthesis 1. The aperture 324 may extend through a length of the prosthesis retention member 318 so that an inner support member 20 can extend distally past the prosthesis retention member 318. In this way, a guide wire 62 can also be directed through the inner support member 20 and/or prosthesis retention member 318. In one example, the distal portion 320 can include two paddle pockets 333 approximately 180 degrees from each other. The distal portion 320 and proximal portion 322 can be connected via a ball joint 328. For example, the distal portion 320 can include a spherical bearing 330 and the proximal portion 322 can include a corresponding socket 332 to receive the bearing 330. In this way, the distal portion 320 can move with three rotational degrees of freedom about the proximal portion 322. When the capsule 232 rotates, the prosthesis retention member 318 and prosthesis 1 can rotate with the capsule 232. The proximal portion 322 can be threadably connected to the inner shaft member 216, for example, which maintains the longitudinal position of the prosthesis retention member 318. The joint formed by the distal and proximal portions 320, 322 has a greater degree of freedom and, therefore, may reduce tension stored in a delivery device during tracking or deployment of a prosthesis. As at least in part indicated with like reference numerals, the delivery device 310 can be otherwise similarly configured and operate identically as compared to other delivery devices disclosed herein except as explicitly stated.

Referring now in addition to FIGS. 24-27 which illustrate select portions of an alternate delivery device 410 including an outer sheath member 414 having a capsule 432 that is rotatable with respect to the outer sheath member 414. In this example, the capsule 432 and the outer sheath member 414 are cooperatively configured so that they can rotate with respect to each other. In one example, the capsule 432 has a coupling portion 424 defining a recess 420 in which a retaining portion 422 of the outer sheath member 414 is maintained. In one example, the retaining portion 422 has a larger outer diameter as compared to an outer diameter of the outer sheath member 414. As indicated above, if the capsule 432 is rotatable with respect to the outer sheath member 414, it may also be desirable for a prosthesis retention member, hub or spindle 418 of the delivery device 410 to be rotatable with respect to an inner shaft member 416 to which it is secured, the inner shaft member 416 being of the type disclosed above with respect to prior embodiments. In one example, the inner shaft member 416, which is positioned at least partially within the outer sheath member 414, includes a coupling portion 430 defining a recess 436 in which a retaining portion 434 of the prosthesis retention member 418 is maintained. In one example, an outer diameter of the retaining portion 434 is greater than an outer diameter of a body 425 of the prosthesis retention member 418. The delivery device 410 can otherwise be identically configured and operate similar to those other delivery devices disclosed herein except as explicitly stated.

Figure 28:
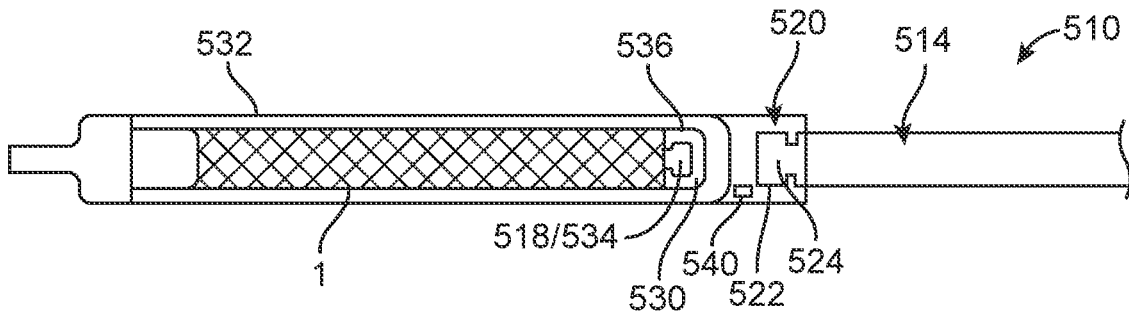
FIG. 28 is a schematic diagram of an alternate delivery device having a capsule that can be manually rotated with a motor.

Referring now to FIG. 28, which illustrates select components of an alternate delivery device 510 including an outer sheath member 514 having a capsule 532. In this example, the capsule 532 and the outer sheath member 514 are cooperatively configured so that the capsule 532 can rotate with respect to the outer sheath member 514. In one example, the capsule 532 has a coupling portion 520 defining a recess 522 in which a retaining portion 524 of the outer sheath member 514 is maintained. In one example, the retaining portion 524 has a larger outer diameter as compared to an outer diameter of the outer sheath member 514. As indicated above, if the capsule 532 is rotatable with respect to the outer sheath member 514, it can also be desirable for a prosthesis retention member, hub or spindle 518 of the delivery device 510 to be rotatable with respect to an inner shaft member 516 to which it is secured, the inner shaft member 516 being at least partially extending through the outer sheath member 514 similar to prior embodiments including an inner shaft member, prosthesis retention member and outer sheath member. In one example, the inner shaft member 516 includes a coupling portion 530 defining a recess 536 in which the retaining portion 534 of the prosthesis retention member 518 is maintained. In this example, the delivery device 510 can include a motor 540 schematically represented) configured to rotate the capsule 532 with respect to the outer sheath member 514. The motor 540 can be wirelessly controlled via a remote or alternative controls on a handle assembly of the delivery device (see handle assembly 12, for example). The delivery device 510 can otherwise be identically configured and operate similar to those other delivery devices disclosed herein except as explicitly stated. The delivery device 510 allows for clocking of the capsule locally without torqueing through the whole anatomy. The ability of clock a prosthesis (e.g., prosthesis 1), via selective rotation of the prosthesis retention member 518, allows the prosthesis to be aligned with the coronary arteries which aids in access for further percutaneous coronary intervention procedures.

Figure 2:
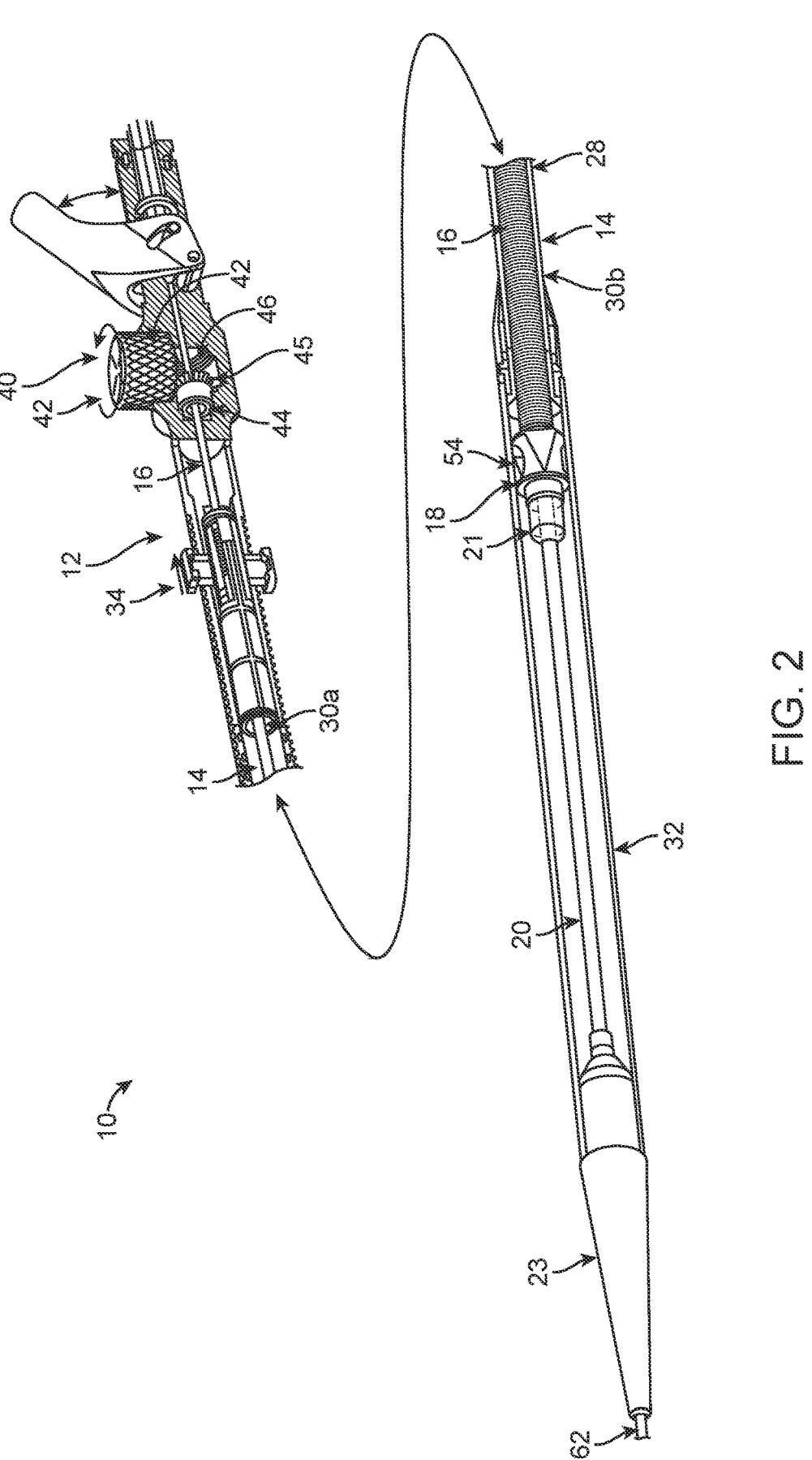
FIG. 2 is a partial, cross-sectional view of the delivery device of FIG. 1.
Figure 3:
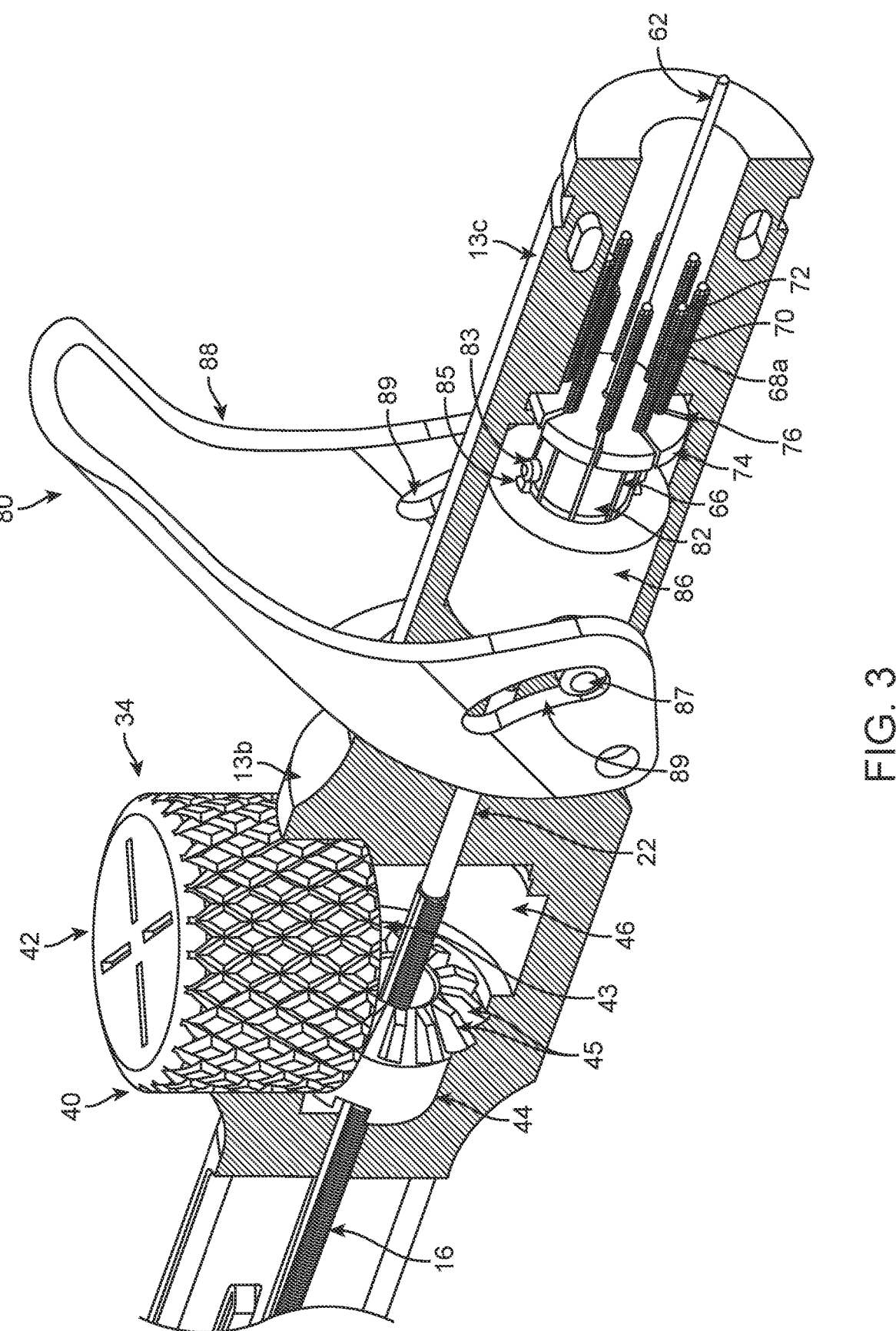
FIG. 3 is a partial, cross-sectional view of the handle assembly of FIGS. 1-2.
Figures 4A, 4B, 5:
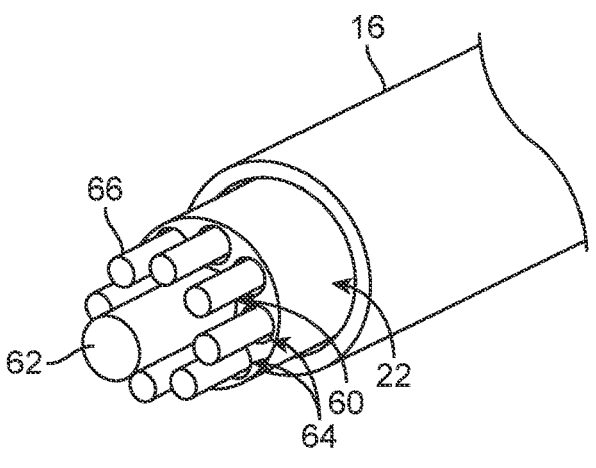
FIGS. 4A-4B are partial, views of select components of the handle assembly of FIGS. 1-3.
FIG. 5 is a partial, perspective view of an inner shaft member of the delivery device of FIGS. 1-4B, including a core member of the inner shaft member including a plurality of tensile wires that can be locked or unlocked by an actuator provided in the handle assembly.
Figure 29:
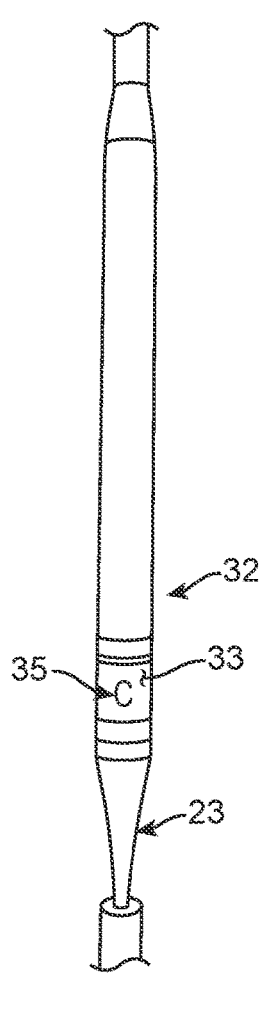
FIG. 29 is a partial, side view of a delivery device having a capsule including at least one echogenic marker.
Figures 30A, 30B, 30C, 30D:
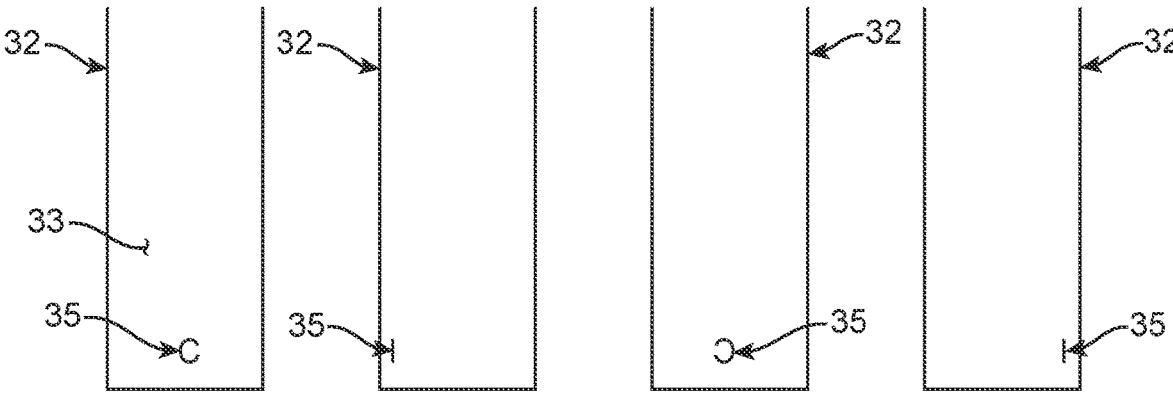
FIGS. 30A-30D are partial, side views of the capsule of FIG. 29 as viewed at four different rotational positions around an outer surface of the capsule.
Figure 31:
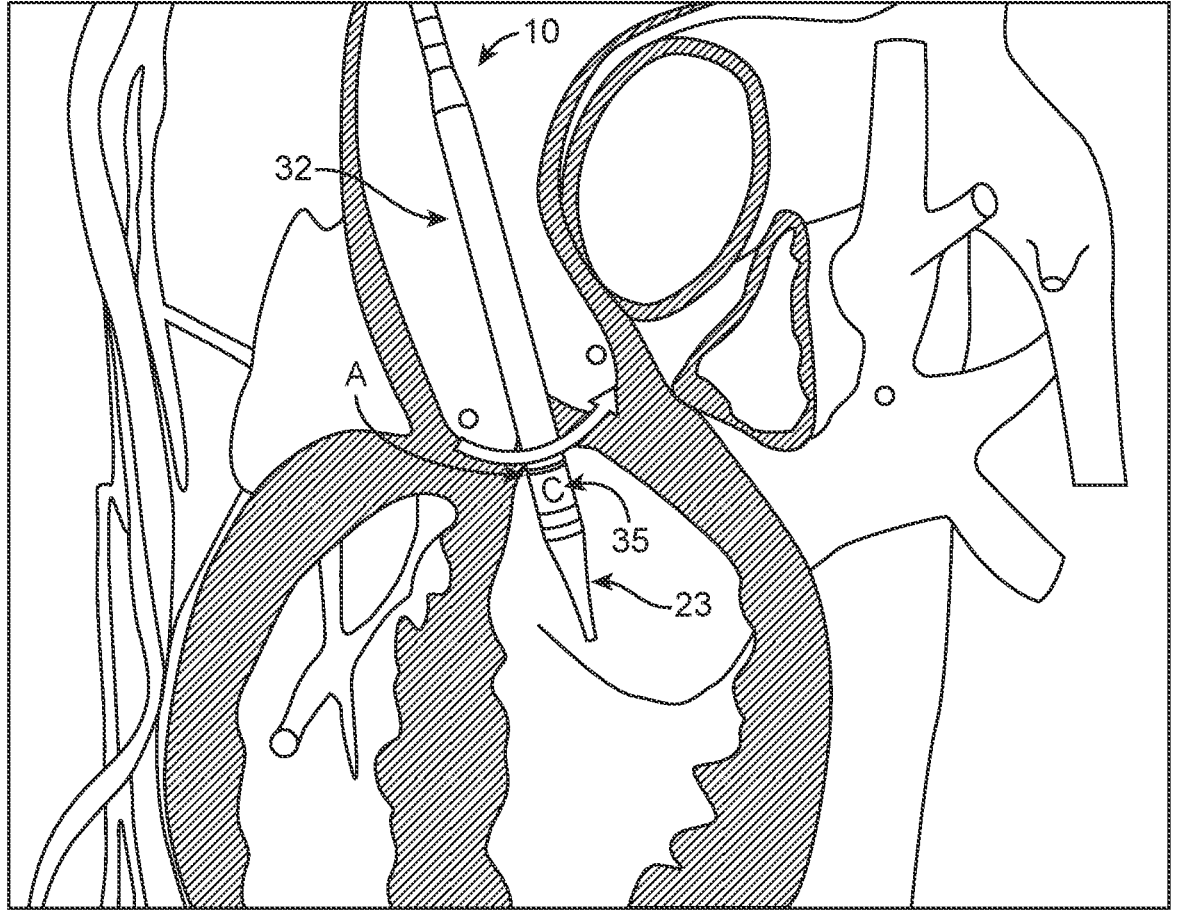
FIG. 31 is a schematic illustration of the capsule of FIGS. 2-30D during delivery.

Referring now in addition to FIGS. 29-31, which illustrate a distal end of the delivery device 10 of FIG. 2 including the capsule 32 having an outer surface 33 and at least one echogenic marker 35 positioned on the outer surface 33. For example, the marker 35 could be applied to or formed within the outer surface 33 in a number of ways including embedding the marker 35 into the material (e.g., polymer or metal) of the capsule 32 or printing the marker 35 on the outer surface 33. Other techniques for forming the echogenic marker(s) 35 are also envisioned and suitable for use with the capsules of the disclosure. Such markers 35 can be aligned with various features of the prosthesis when the prosthesis is loaded within the capsule 32. For example, the marker 35 can be aligned with a commissure or cusp of the prosthesis. During delivery, the marker 35 can be viewed under fluoroscopy to indicate the rotation of the prosthesis (contained within the capsule 32) and/or the capsule 32 relative to a feature on the patient's anatomy which could be, but is not limited to, a patient's native coronary ostia or valve commissure.

In various examples, each marker 35 is shaped such that the marker 35 can be clearly distinguished whether each respective marker 35 is located anterior, posterior or from the side. One non-limiting example is a "C" shaped marker 35, which is illustrated, however the concept is not limited to this particular shape. Such marker(s) can be incorporated into any capsule of the present disclosure.

The marker(s) 35 is particularly beneficial with delivery devices of the disclosure in which the distal end of the delivery device, including the prosthesis, are rotated prior to deployment of the prosthesis to properly locate and orient the prosthesis with respect to the anatomy. Such alignment can include, but is not limited to, aligning enlarged cells in the prosthesis frame with native coronary ostia and/or aligning commissures of the prosthesis away from native coronary ostia and, for example, with the native commissures. The marker(s) 35 allow for the physician to visualize the rotational orientation of the prosthesis during delivery to ensure proper deployment placement. In the illustrated example of FIG. 31, the loaded delivery device is directed to an aortic valve annulus A (see also, for example, FIG. 24 and related disclosure). It will be understood that the annulus need not be an aortic valve annulus and that this example is merely illustrative. The capsule 32 is viewed under fluoroscopy when the capsule 32 is at or is approaching the annulus A and an orientation of the marker(s) 35 are determined to correspondingly determine an orientation of the prosthesis (not visible) loaded within the capsule 32. If desired, the distal end (e.g., capsule 32) of the delivery device 10 is rotated about its central axis within the valve annulus to reorient the capsule 32 and prosthesis until the marker(s) 35 are aligned with features of the anatomy as discussed above. Rotation of the distal end of the delivery device and/or capsule 32 can be accomplished in any manner disclosed herein. Once the rotational position of the capsule 32 and prosthesis are as desired, the prosthesis can be deployed from the capsule 32.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A delivery device comprising:
an outer sheath member having a distal end and a proximal end;
a tensile resistance actuator provided proximate the proximal end of the outer sheath member;
an inner shaft member defining a plurality of lumens;
a prosthesis retention member connected to the inner shaft member and configured to retain a prosthesis;
a coupling comprising a distal end disposed within a cavity of the prosthesis retention member and extending proximally from the prosthesis retention member, wherein the prosthesis retention member is configured to freely rotate about the distal end of the coupling, while maintaining the distal end of the coupling within the cavity; and
a plurality of tensile wires, each of the tensile wires slidably positioned within one of the plurality of lumens of the inner shaft member, wherein each of the tensile wires are secured to the coupling and the tensile resistance actuator;
wherein the delivery device has an unlocked configuration in which a length of the tensile wire between the coupling and the tensile resistance actuator is variable;
further wherein the delivery device has a locked configuration in which the length of each tensile wire between the coupling and the tensile resistance actuator is invariable.

2. The delivery device of claim 1, further comprising a handle assembly connected to the proximal end of the outer sheath member.

3. The delivery device of claim 2, further comprising a torque coil positioned within the outer sheath member and extending over the inner shaft member from the handle assembly to the coupling.

4. The delivery device of claim 3, wherein the handle assembly includes a torque coil actuator configured to rotate the torque coil about a longitudinal axis of the torque coil with respect to the inner shaft member.

5. The delivery device of claim 2, wherein the tensile resistance actuator is positioned at least partially within the handle assembly and is rotatable with respect to the handle assembly.

6. The delivery device of claim 2, wherein the handle assembly includes a tapered surface over which the tensile wires are routed.

7. The delivery device of claim 2, wherein the inner shaft member is rotatably coupled about a longitudinal axis of the inner shaft member with respect to the handle assembly.

8. The delivery device of claim 1, wherein the tensile resistance actuator is configured to compressively maintain a position of the tensile wires when the delivery device is in the locked configuration.

9. The delivery device of claim 1, wherein the prosthesis retention member has a first portion and a second portion, the first portion being rotatable with respect to the second portion.

10. The delivery device of claim 9, wherein the first portion of the prosthesis retention member and the second portion of the prosthesis retention member are coupled to one another with a ball and socket joint.

11. The delivery device of claim 1, wherein the inner shaft member includes a central lumen.

12. The delivery device of any claim 1, wherein the prosthesis retention member is configured to rotate about a longitudinal axis of the prosthesis retention member with respect to the inner shaft member.

13. The delivery device of claim 12, wherein the outer sheath member includes a capsule and a body; wherein the capsule is rotatable with respect to the body.

14. The delivery device of claim 12, wherein the prosthesis retention member fits over a bearing chassis that is connected to the inner shaft member.

15. The delivery device of claim 1, wherein the tensile resistance actuator includes a pivotal lever.

16. The delivery device of claim 1, wherein the outer sheath member includes a body and a capsule connected to the body at the distal end of the outer sheath member, wherein the capsule can rotate about a longitudinal axis of the outer sheath member with respect to the body.

17. The delivery device of claim 16, wherein the capsule includes an outer surface and an echogenic marker on the outer surface.

18. The delivery device of claim 1, wherein at least one biasing element places tension in at least one of the tensile wires in the unlocked configuration.

19. The delivery device of claim 18, wherein each tensile wire is tensioned by a respective biasing element in the unlocked configuration.

20. A delivery device comprising:
an outer sheath member having a distal end and a proximal end;
a tensile resistance actuator provided proximate the proximal end of the outer sheath member;
an inner shaft member defining a plurality of lumens;
a coupling proximate the distal end of the outer sheath member and positioned radially inward relative to the inner shaft member;
a prosthesis retention member connected to the inner shaft member and configured to retain a prosthesis, wherein the prosthesis retention member is configured to freely rotate about a distal end portion of the coupling, while maintaining an axial position along a longitudinal axis of the coupling; and
a plurality of tensile wires, each of the tensile wires slidably positioned within one of the plurality of lumens of the inner shaft member, wherein each of the tensile wires are secured to the coupling and the tensile resistance actuator;
wherein the delivery device has an unlocked configuration in which a length of the tensile wire between the coupling and the tensile resistance actuator is variable;
further wherein the delivery device has a locked configuration in which the length of each tensile wire between the coupling and the tensile resistance actuator is invariable.

* * * * *